United States Patent [19]

Bock et al.

[11] 4,288,586

[45] Sep. 8, 1981

[54] PROCESS FOR THE PREPARATION OF POLYISOCYANATES CONTAINING ISOCYANURATE GROUPS

[75] Inventors: Manfred Bock, Leverkusen; Josef Pedain; Wilhelm Slawyk, both of Cologne, all of Fed. Rep. of Germany

[73] Assignee: Bayer Aktiengesellschaft, Leverkusen, Fed. Rep. of Germany

[21] Appl. No.: 11,465

[22] Filed: Feb. 12, 1979

[30] Foreign Application Priority Data

Feb. 17, 1978 [DE]  Fed. Rep. of Germany ....... 2806731

[51] Int. Cl.³ ............... C08G 18/79; C08G 18/80; C08G 18/16

[52] U.S. Cl. ................. 528/67; 260/453 P; 528/44; 528/45; 528/52; 528/53; 528/54; 528/55; 528/56; 528/58; 528/73; 528/67; 528/51

[58] Field of Search ............ 528/52, 44, 67, 73, 528/45; 260/453 P

[56] References Cited

U.S. PATENT DOCUMENTS

| | | | |
|---|---|---|---|
| 3,042,632 | 8/1962 | Erner | 521/129 |
| 3,108,100 | 10/1963 | Tate et al. | 528/52 |
| 3,183,112 | 5/1965 | Gemassmer | 528/44 |
| 3,457,291 | 7/1969 | Baylor | 528/44 |
| 3,471,543 | 10/1969 | Sayigh | 528/44 |
| 3,487,080 | 12/1969 | Matsui et al. | 528/52 |
| 3,583,943 | 6/1971 | Weber et al. | 528/73 |
| 3,892,687 | 7/1975 | Bechara et al. | 528/52 |
| 3,919,218 | 11/1975 | Schmitt et al. | 528/52 |
| 4,115,373 | 11/1978 | Henes et al. | 528/48 |

FOREIGN PATENT DOCUMENTS

| | | |
|---|---|---|
| 1150080 | 6/1963 | Fed. Rep. of Germany . |
| 1934763 | 1/1971 | Fed. Rep. of Germany . |
| 2631733 | 2/1977 | Fed. Rep. of Germany . |
| 1386399 | 3/1975 | United Kingdom . |
| 1391066 | 4/1975 | United Kingdom . |
| 1465812 | 3/1977 | United Kingdom . |

*Primary Examiner*—H. S. Cockeram
*Attorney, Agent, or Firm*—Gene Harsh; Lawrence S. Pope; Thomas W. Roy

[57] ABSTRACT

The present invention relates to a new process for the preparation of polyisocyanates containing isocyanurate groups by the partial trimerization of the isocyanate groups of 1-isocyanato-3,3,5-trimethyl-5-isocyanatomethyl-cyclohexane (also known as isophorone diisocyanate and abbreviated IPDI), using catalysts which accelerate the trimerization of isocyanate groups, characterized in that the catalysts used are quaternary hydroxyalkyl ammonium hydroxides containing at least one hydroxyalkyl group. The present invention also relates to the polyisocyanates containing isocyanurate groups produced according to this process and to their use, optionally in the form of products which are blocked with blocking agents for isocyanate groups, as isocyanate components for polyurethane lacquers.

12 Claims, No Drawings

PROCESS FOR THE PREPARATION OF POLYISOCYANATES CONTAINING ISOCYANURATE GROUPS

BACKGROUND OF THE INVENTION

The cyclopolymerization of IPDI is already known. According to German Published Patent Application No. 1,934,763, a reaction mixture which contains polyisocyanates with isocyanurate groups in addition to the dimerization product is formed when phosphines are used as catalysts.

British Pat. Nos. 1,391,066 and 1,386,399 describe the polymerization of IPDI using alkali metal phenolates as catalysts. The use of such catalysts has the advantage over catalysis with phosphines that the reaction products consist almost entirely of trimers and virtually no dimerized polyisocyanates are formed. However, the use of such catalysts had serious disadvantages, as explained below.

The polymerization reaction is very vigorous and it is presumably for this reason that in all of the examples given, the reaction is carried out in the presence of a solvent.

Separation of unreacted free IPDI proves to be extremely difficult because the polymerization products are not uniform and have a high viscosity. Furthermore, the catalyst must be neutralized to terminate the reaction, and this causes cloudiness due to the resulting salts. The use of the products of British Pat. No. 1,386,399 in the production of lacquers is consequently very difficult if not impossible.

There have therefore been many attempts to improve further the desired polymerization of IPDI. German Published Patent Application No. 2,325,826 and its equivalent U.S. Pat. No. 3,919,218 discloses a process for the preparation of stable isocyanato-isocyanurate solutions in which IPDI is used, inter alia, as a starting material. In this process, aziridine or an aziridine derivative in combination with a tertiary amine is used as the catalyst. This process has the disadvantages that aziridine is dangerous to handle because of its well-known carcinogenic properties and that a part of the catalyst must be removed by distillation. Moreover, polymerization carried out by this process has an incubation period of several hours, during which time the diisocyanate must be heated. When the exothermic reaction finally begins, the temperature rises sharply within a few minutes. A solvent must be added to the reaction mixture to prevent excessive turbulence. Moreover, since this process takes several hours, it is considered time consuming.

A commercially viable, simple process for the production of polyisocyanates containing isocyanurate groups from IPDI is unavailable, for the reasons given above. Since, a substantially colorless polyisocyanate containing isocyanurate groups based on IPDI and free from solvents and substantially free from monomers would be an extremely interesting polyisocyanate for lacquers, it was an object of the present invention to provide such a process.

This problem could surprisingly be solved by using quite specific quaternary ammonium hydroxides as catalysts for the trimerization of IPDI.

The use of quaternary ammonium hydroxides as trimerization catalysts for isocyanates has already been disclosed in German Pat. No. 1,150,080, but the ammonium hydroxides disclosed in the said publication are hardly suitable as commercial catalysts, in particular for the solvent-free trimerization of IPDI, because the reaction is not controllable in the absence of solvents. When attempts are made to trimerize aliphatic or cycloaliphatic diisocyanates with the ammonium hydroxides mentioned in the aforesaid publication, a sudden vigorous exothermic reaction is frequently observed after a substantial incubation time. The examples given in German Pat. No. 1,150,080, therefore, mainly describe only the trimerization of aromatic isocyanates. The only example of the trimerization of an aliphatic isocyanate is the trimerization of hexadecyl isocyanate mentioned in Example 13. After a reaction time of 4 days, the corresponding trimer is obtained in a yield of less than 50%. The catalysts given in German Pat. No. 1,150,080 are unsuitable for economical solvent-free trimerization of IPDI by a reproducible and easily controlled reaction.

The quaternary ammonium salts, ammonium alcoholates and ammonium phenolates mentioned in German Published Patent Application 2,631,733 (equivalent U.S. Pat. No. 4,040,992) and in British Pat. No. 1,465,812 are also unsuitable as catalysts for such a reaction because the compounds are not easily destroyed by heat and must therefore be inactivated by the addition of a catalyst poison when the desired degree of trimerization has been reached which again leads to undesirable impurities in the end product.

The catalysts to be used according to the invention, on the other hand, make it possible for polyisocyanates containing isocyanurate groups to be obtained from IPDI without the use of solvents, and inactivation of the catalyst, for example by the addition of a catalyst poison, is unnecessary since the compounds used according to the invention as catalysts are decomposed by heat during the reaction, thereby losing their activity.

SUMMARY OF THE INVENTION

The present invention relates to a process for the preparation of polyisocyanates containing isocyanurate groups by the partial trimerization of the isocyanate groups of 1-isocyanato-3,3-trimethyl-5-isocyanatomethyl-cyclohexane, using catalysts which accelerate the trimerization of isocyanate groups, characterized in that the catalysts used are quaternary hydroxyalkyl ammonium hydroxides containing at least one hydroxyalkyl group.

The present invention also relates to the polyisocyanates containing isocyanurate groups produced according to this process and to their use, optionally in the form of products which are blocked with blocking agents for isocyanate groups, as isocyanate components in a process for the production of polyurethane lacquers.

DETAILED DESCRIPTION OF THE INVENTION

The quaternary ammonium hydroxides containing at least one hydroxyalkyl group which are suitable as catalysts according to the invention may be any compounds of this type, for example those corresponding to the following formula:

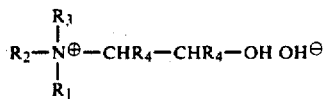

in which

R$_1$, R$_2$ and R$_3$ which may be the same or different, represent alkyl groups with about 1 to 20 carbon atoms which may be substituted with hydroxyl groups, cycloalkyl groups with about 4 to 15 carbon atoms which may be substituted with hydroxyl groups, aralkyl groups with about 7 to 15 carbon atoms which may be substituted with hydroxyl groups or aryl groups with about 6 to 15 carbon atoms which may be substituted with hydroxyl groups, and two of the aforesaid groups R$_1$, R$_2$ and R$_3$ may also combine with the nitrogen atom and optionally with an oxygen atom or another nitrogen hetero atom to form a heterocyclic ring containing about 4 to 6 carbon atoms, the groups R$_1$, R$_2$ and R$_3$ each representing ethylene groups which form a bicyclic triethylene diamine structure together with the quarternary nitrogen atom and another tertiary nitrogen atom;

R$_4$ represents hydrogen and/or an alkyl group with about 1 to 12 carbon atoms, a cycloalkyl group with about 5 to 7 carbon atoms, an aralkyl group with about 7 to 10 carbon atoms, an aryl group with about 6 to 12 carbon atoms or a group of the formula R$_5$—O—(CH$_2$)$_n$ in which R$_5$ represents hydrogen, an alkyl group with about 1 to 12 carbon atoms, a cycloalkyl group with about 4 to 10 carbon atoms, an aralkyl group with about 7 to 10 carbon atoms or an aryl group with about 6 to 10 carbon atoms and n is an integer of from about 1 to 6.

The preferred catalysts to be used according to the invention include compounds of the above-mentioned formula wherein R$_1$, R$_2$ and R$_3$ represent the same or different alkyl groups having from about 1 to 4 carbon atoms and R$_4$ represents hydrogen.

A particularly preferred catalyst is N,N,N-trimethyl-N-(2-hydroxyethyl)-ammonium hydroxide.

Compounds which are suitable as catalysts for the process according to the invention are prepared from tertiary amines such as, for example, trimethylamine; tributylamine; 2-dimethylamino ethanol; triethanolamine; dodecyl dimethylamine; N,N-dimethyl cyclohexylamine; N-methyl pyrrolidine; N-methyl morpholine or 1,4-diazabicyclo-2,2,2-octane and alkylene oxides such as ethylene oxide, propylene oxide, butylene oxide-(1,2), styrene oxide or methoxy-, ethoxy- or phenoxy-propylene oxide.

The catalysts are prepared in known manner by the reaction of alkylene oxide and tertiary amine in an aqueous-alcoholic medium (see U.S. Pat. No. 3,995,997, column 2, lines 19–44). Suitable alcohols include, for example, methanol, ethanol, propanol and tertiary butanol. Distillable components, such as water or the tertiary butanol which does not take part in the reaction with alkylene oxide, are subsequently removed. The amount of quaternary base present is determined analytically, for example by titration, so that the quantity required for trimerization can be determined.

The catalysts are generally used in a quantity of from about 0.01 to 1% by weight, preferably about 0.03 to 0.3% by weight, based on the quantity of IPDI put into the reaction. They may be used in the pure form or as solutions. Suitable solvents are, for example, toluene, dimethyl formamide, dimethyl sulphoxide or mixtures of these solvents, depending on the nature of the catalyst. If hydroxyl compounds which form carbamic acid derivatives are used as co-catalysts (see below), it is advantageous to use these same hydroxyl compounds as solvents for the catalysts. Suitable co-catalysts of this type include, for example, methanol, ethanol, 2-ethylhexanol and glycols such as ethane diol, butane diol or 2-ethyl-hexane diol.

The process according to the invention has various fundamental advantages. With suitable control of the quantity of catalyst, trimerization proceeds slowly and steadily, without an incubation period. The solvents may therefore be dispensed with. If trimerization has not progressed sufficiently far, fresh catalyst may be added and the reaction continued until the desired degree of trimerization has been reached; this is not easily possible by the trimerization processes known in the art. Owing to the thermal instability of the catalysts, there is no need to stop the trimerization reaction by catalyst inhibitors. Unwanted cloudiness due to salt formation when catalyst inhibitors are used does not therefore occur in the trimerization products even when they are highly diluted. Another advantage of the thermal instability of the catalysts used according to the invention is that uncontrolled complete polymerization of the reaction mixture is virtually impossible because the sharp increase in temperature which would occur in such a case would automatically destroy the catalyst and thereby stop the reaction.

The addition of co-catalysts is possible but not necessary in the process according to the invention. Substances which may be used as co-catalysts are of the type which are known to polymerize isocyanates. They may be used in quantities of from about 1 to 90% by weight, preferably about 1 to 50% by weight, of the catalyst used. The following are examples of suitable catalysts: tertiary amines such as triethylamine, tributylamine, N-metyl-morpholine, N-ethylmorpholine, N-cocomorpholine, N,N,N',N'-tetramethyl-ethylene diamine, 1,4-diaza-bicyclo-(2,2,2)-octane, N-methyl-N'-dimethyl-aminoethyl-piperazine, N,N-dimethyl benzylamine, bis-(N,N-diethylaminoethyl)-adipate, N,N-diethyl benzylamine, pentamethyl diethylene triamine, N,N-dimethyl-cyclohexylamine, N,N,N',N'-tetramethyl-1,3-butane diamine, N,N-dimethyl-β-phenyl ethylamine, 1,2-dimethyl imidazole and 2-methyl imidazole.

Mannich bases of secondary amines such as dimethylamine, diethylamine or morpholine and aldehydes, particularly formaldehyde or ketones such as acetone, methylethyl ketone or cyclohexanone and phenols such as phenol, nonyl phenol or bisphenol are also suitable as co-catalysts. As additional catalysts there may also be used various tertiary amines which contain isocyanate reactive hydrogen atoms, for example triethanolamine, triisopropanolamine, N-methyl-diethanolamine, N,N-dimethyl ethanolamine and their reaction products with alkylene oxides such as propylene oxide and/or ethylene oxide. Aliphatic, araliphatic and mixed aliphatic-aromatic phosphines may also be used as co-catalysts, e.g. triethyl phosphine, tri-n-butyl phosphine, dimethyl benzyl phosphine, dimethyl phenyl phosphine, tribenzyl phosphine or p-butylphosphacyclopentane.

Silaamines containing carbon-silicon bonds of the types described e.g. in German Pat. No. 1,229,290 which corresponds to British Pat. No. 1,090,589 are also suitable, e.g. 2,2,4-trimethyl-2-silamorpholine or 1,3-diethylaminomethyltetramethyl-disiloxane.

Carbamic acid esters may also be used, analogously to British Pat. No. 949,253 or German Pat. No. 1,013,869. These carbamic esters are prepared by the reaction of aliphatic, araliphatic or aromatic mono or polyhydroxyl compounds with mono or polyisocyanates, preferably with the IPDI used here. It is immaterial to the course of polymerization whether a preformed and isolated carbamic acid ester is added to the IPDI which is to be polymerized or whether the carbamic acid ester is formed in situ during the trimerization reaction, as for example when the hydroxyl compound is introduced into the isocyanate together with the catalyst, possibly as a solution. Suitable hydroxyl compounds which react with IPDI to form carbamic acid derivatives which are active as co-catalysts and at the same time are effective solvents for the quarternary nitrogen bases which are the true trimerization catalysts include, for example, methanol, ethanol, 2-ethyl hexanol and glycols such as ethane diol, butane diol or 2-ethyl-hexane diol. Apart from these co-catalysts, other substances which are basic in reaction may be used, such as alkali metal and alkaline earth metal hydroxides, alkali metal alcoholates and phenolates, and alkali metal and alkaline earth metal salts of carboxylic acids and of higher fatty acids.

It is, of course, also possible to use mixtures of various co-catalysts or to use other catalyst systems which are capable of accelerating the isocyanate reactions, such as organometallic compounds of tin, antimony or lead. It is preferred, however, to use co-catalysts which are chemically built in at the stage of trimerization, such as hydroxyl compounds which form carbamic acid derivatives or those which, like the related trimerization catalysts, can be inactivated by heat, for example Mannich bases.

The starting material used for the process according to the invention is preferably commercially pure, i.e. distilled and colorless IPDI.

The reaction according to the invention is carried out at temperatures between about 30° and 90° C., preferably between about 40° and 80° C. It is generally carried out solvent-free, apart from the small quantities of solvents used for the catalyst, although the possibility of using the known lacquer solvents is, of course, not excluded in principle.

It is one of the main advantages of the catalysts to be used according to the invention that they develop their activity immediately, i.e. without incubation. At the same time, the catalysts used according to the invention begin to be decomposed by heat at the given temperature ranges so that the degree of trimerization which is the percentage of trimerized isocyanate groups based on the total quantity of isocyanate groups originally present, at a given starting temperature can easily be controlled by the quantity of catalyst added. If desired, the degree of trimerization may also be further increased by the addition of a further quantity of catalyst after the first quantity has been decomposed by heat.

The quantity of catalyst is generally calculated to produce a reaction mixture, without solvent, having an isocyanate content of about 25 to 35% by weight, preferably about 27 to 32% by weight. Unreacted excess IPDI may subsequently be removed in known manner, for example by thin layer distillation.

The process according to the invention may, for example, be carried out as follows:

IPDI is introduced into a three-necked flask under nitrogen (the presence of inert gas is not absolutely necessary) and heated to a temperature in the range of from about 40° to 70° C., for example 50° C. The catalyst solution is then added. Trimerization begins as soon as the catalyst solution has been stirred into the IPDI. The temperature slowly rises to about 70° to 80° C. within about 30 to 60 minutes. Stirring is continued at this temperature for approximately one hour, during which time the catalyst becomes inactivated due to its thermal instability. The solution of trimer is then freed from excess IPDI in a high vacuum (thin layer distillation). Depending on the degree of trimerization, the product according to the invention is obtained as a distillation residue in the form of a pale yellow, brittle resin which, when dissolved at a concentration of about 75% by weight in ethylglycol acetate has a viscosity of at the most about 50,000 mPas at 25° C., preferably less than about 20,000 mPas, an isocyanate content of about 9.5 to 15.5% by weight, preferably about 11 to 14% by weight, and a free IPDI content of below, about 3% by weight, preferably below about 1% by weight.

A major factor which determines the quality of the end product (viscosity of the resin solution) is the careful conditions under which trimerization takes place. The quantity of catalyst is therefore calculated to ensure that the reaction does not progress too rapidly. It is therefore also advantageous to add the catalyst solution in two or more stages. As already described above, the IPDI is first heated to a suitable starting temperature, for example about 60° C. A portion of the catalyst solution, for example half to two-thirds of the total quantity, is then run in. The temperature rises at the onset of trimerization and reaches its first maximum after about 15 to 30 minutes. Stirring is continued at this temperature until the reaction dies down, at which point a further portion of catalyst solution is added. The temperature then again rises to reach 80° C. after about 15 minutes. After further stirring, the isocyanate content becomes constant and does not substantially fall even after prolonged stirring. If the desired isocyanate content has not been completely reached in the trimer solution at this point, the end point can be adjusted by further addition of catalyst at about 80° C. This subsequent catalysis is carried out at a temperature of from about 80° to 85° C., maximum about 90° C. It has proved to be particularly advantageous for the quality of the end products to continue trimerization until the reaction mixture, which still contains excess IPDI, has an isocyanate content of about 30±1% by weight. This can easily be adjusted by the method described here. As soon as this isocyanate content is reached, stirring is continued for half an hour and the excess IPDI is then distilled off in a high vacuum. Another factor which favors slow, progressive trimerization is the steady, constant addition of catalyst solution to the reaction mixture containing IPDI until the desired isocyanate content has been reached. This method is particularly suitable for large batches in which a very uniform rate of addition of solution can be achieved by means of metering pumps.

In another embodiment of the process, full use is made of the inactivity of the catalyst solution towards IPDI at room temperature. A mixture of IPDI and catalyst solution in suitable proportions for trimerization is stable for a considerable time at about 20° to 25° C., and trimerization only sets in at elevated temperatures. In this case, the above mentioned mixture is introduced into the reaction mixture heated to temperatures of from about 60° to 90° C., for example about 75° C., either by means of the delivery pump or, in the case of smaller batches, by means of a dropping funnel. The isocyanate content of the trimer solution soon becomes established at a steady value which depends on the proportion of catalyst to IPDI and remains constant during the whole time of addition of the mixture. The solution can be adjusted to a particular isocyanate value by varying the catalyst concentration. The very moderate conditions of this procedure result in a lightly colored trimer whose 75% solution in ethylglycol acetate has a low viscosity.

When a co-catalyst is also used, it is stirred into the IPDI before the trimerization reaction or added together with the trimerization catalyst. In that case, the polymerization reaction may also be carried out according to the alternatives mentioned above, the catalyst solution being added as a single dose, portionwise or continuously. It has already been mentioned that since the catalysts used can be inactivated by heat, it is not necessary although possible to stop this reaction with the usual alkylating substances used for the purpose. This is, of course, necessary if a co-catalyst which is not inactivated by heat is used.

Trimerization of IPDI may also be carried out continuously in a cascade of vessels by a similar course of reaction and using the same catalysts. In this case, it is also advantageous to be able to stop the reaction by heat.

The process according to the invention has the following important advantages compared with the known art processes:

1. The process is easily controlled at every phase because the catalysts used according to the invention develop their activity without an incubation period and because they are thermally labile substances which decompose at the reaction temperatures so that they do not need to be inactivated by the addition of a catalyst poison.

2. In the process according to the invention, trimerization can be adjusted to particular end values by subsequent additional catalysis so that products of consistent quality can be produced.

3. The process is technically easy to carry out and inexpensive.

4. The process provides a means of producing modified polyisocyanates which are light in color, readily soluble in the usual lacquer solvents, easily freed from excess IPDI and physiologically substantially harmless.

The products according to the invention are valuable starting materials for the production of polyurethane resins by the isocyanate polyaddition process, in particular for the production of one component or two component polyurethane lacquers.

The products according to the invention blocked with known blocking agents are valuable starting materials for two component polyurethane stoving lacquers.

When the products of the process according to the invention, optionally in their blocked form, are to be used for the production of polyurethane lacquers, the substances with which they are reacted are preferably the polyhydroxy polyesters, in particular alkyd resins, and polydihydroxy polyacrylates used in the technology of polyurethane lacquers and optionally low molecular weight, polyhydric alcohols. Polyamines, particularly when blocked in the form of polyketimines or oxazolidines, could also be used as reactants for the products according to the invention. The proportions in which the blocked or unblocked polyisocyanates according to the invention and the above mentioned reactants are used for the production of polyurethane lacquers are generally chosen to provide from about 0.8 to 3, preferably from about 0.9 to 1.1 hydroxyl, amino and/or carboxyl groups to 1 isocyanate group which may be blocked.

The usual catalysts of isocyanate chemistry may be used to accelerate hardening in known manner, e.g. tertiary amines such as triethylamine, pyridine, methyl pyridine, benzyl dimethylamine, N,N-dimethyl aminocyclo hexane, N-methyl piperidine, pentamethyl diethylene triamine, N,N'-endoethylene piperazine or N,N'-dimethyl piperazine, or metal salts such as iron-(III) chloride, zinc chloride, zinc-2-ethyl caproate, tin-(II)-2-ethyl caproate, dibutyltin-(IV)-dilaurate or molybdenum glycolate.

When the products according to the invention are used in stoving lacquers, the isocyanate groups are partly or completely blocked in known manner. The polyisocyanate is reacted with a suitable blocking agent, preferably at an elevated temperature, e.g. about 40° to 140° C., optionally in the presence of a suitable catalyst such as a tertiary amine, a metal salt such as zinc-2-ethyl caproate, tin(II)-2-ethyl caproate or dibutyl tin(IV)-dilaurate or an alkali metal phenolate.

The following are examples of suitable blocking agents: monophenols such as phenol, cresols, trimethyl phenols and tertiary butyl phenols; tertiary alcohols such as tertiary butanol, tertiary amyl alcohol or dimethyl phenyl carbonol; compounds which readily form enols, such as ethyl acetoacetate, acetyl acetone or malonic acid derivatives such as malonic acid diesters which have from 1 to 8 carbon atoms in the alcohol groups; secondary aromatic amines such as N-methyl aniline, the N-methyl toluidines, N-phenyl toluidine or N-phenyl xylidine; imides such as succinimide; lactams such as ε-caprolactam or δ-valerolactam; oximes such as butanone oxime or cyclohexanone oxime; mercaptans such as methyl mercaptan, ethyl mercaptan, butyl mercaptan, 2-mercapto benzothiazole, α-naphthyl mercaptan, dodecyl mercaptan, or triazoles such as 1H-1,2,4-triazole.

To prepare lacquer binders, blocked or unblocked polyisocyanate, polyfunctional reactants, catalyst and optionally the usual additives such as pigments, dyes, fillers and levelling agents are vigorously mixed together in the usual mixing apparatus, e.g. a sand mill, either with or without solvent or diluent, and homogenized.

The paints or coatings may be applied to the work pieces as solutions or in the molten or solid form by the usual methods such as brush coating, roller coating, casting, spraying, whirl sintering or the electrostatic powder spray process.

The lacquers containing the polyisocyanates according to the invention give rise to films which adhere surprisingly firmly to metal surfaces, are exceptionally light-fast, resistant to discoloration by heat and highly abrasion resistant and, when used in air-drying lacquers, become surface dry very rapidly even at temperatures around 0° C. In addition, they are distinguished by great hardness, elasticity and chemical resistance, high gloss, excellent weather resistance and a good pigment affinity.

The following examples serve to explain the invention. All percentages given are percentages by weight.

In the following examples 1 to 9 and 11, the following catalyst solutions prepared according to U.S. Pat. No. 3,995,997 were used:

Catalyst Solution I

2-Hydroxy ethyl-trimethyl ammonium hydroxide prepared by ethoxylation of trimethylamine in water/methanol (volumetric ratio 1:1) at about 40° C. and diluted to a 6% by weight solution with dimethyl formamide/methanol (volumetric ratio 4:1).

Catalyst Solution I-a

The same as Catalyst Solution I but using 2-ethyl hexanol/methanol (4:1) instead of dimethyl formamide/methanol (4:1).

Catalyst Solution II

2-Hydroxy ethyl-dodecyl-dimethyl ammonium hydroxide by ethoxylation of dodecyl-dimethylamine in water/methanol at about 40° C., diluted to a 7.5% solution with a 4:1 mixture of dimethyl formamide/methanol.

Catalyst Solution III

Mono adduct of ethylene oxide and 1,4-diazabicyclo-2,2,2-octane obtained by the reaction of 1,4-diazabicyclo-2,2,2-octane with ethylene oxide in water/methanol at about 40° C. and diluted with dimethyl formamide/methanol (4:1) to an 8% solution.

Catalyst Solution IV

2-Hydroxyethyl-dimethyl-2,2'-dihydroxy methylbutyl ammonium hydroxide from dimethyl-2,2'-dihydroxy methylbutylamine, ethylene oxide, water and methanol, diluted to a 20% solution with methanol.

EXAMPLES

Example 1

1332 g (6 mol) of IPDI are heated to 80° C. in a three-necked flask. 15 ml of catalyst solution I are steadily and slowly added dropwise over 45 minutes from a dropping funnel. The temperature rises to about 88° C. during this time (90° C. should not be exceeded. If the temperature is too high, trimerization is not specific and results in higher viscosities in the end product.). Stirring is continued for half an hour after all of the catalyst has been added, the temperature falling to 80° C. The isocyanate content of the trimer solution is then 30.6%. Thin layer evaporation is carried out in a high vacuum and the resin is subsequently dissolved to form a 75% solution in ethyl glycol acetate.

Yield (resin): 580 g (44%).
Viscosity (solution): 5107 mPas (25° C.).
NCO-content (solution): 12.5%.
Free IPDI (solution): 0.18%.

Example 2

1332 g (6 mol) of IPDI are introduced into a three-necked flask and heated to 50° C. 10 ml of catalyst solution I-a are run in from a dropping funnel. The temperature rises to 75° C. within about 30 minutes. It is then raised to 80° C. and stirring is continued at this temperature for half an hour. The isocyanate content of the solution is then 31.1%. Excess IPDI is removed by thin layer distillation and the resin obtained is dissolved to form a 75% solution in ethyl glycol acetate.

Yield (resin): 485 g (39%).
Viscosity (solution): 5550 cP (25° C.).
NCO-content (solution): 12.5%.
Free IPDI (solution): 0.23%.

Example 3

1332 g (6 mol) of IPDI and 1 g of a Mannich base corresponding to the following formula

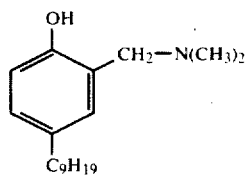

are stirred together at room temperature and heated to 80° C. 15 ml of catalyst solution I are steadily added dropwise from a dropping funnel within about 60 minutes. The temperature slowly rises to 85° C. during this time. This elevated temperature is maintained by dropwise addition of catalyst solution. After termination of the trimerization reaction, stirring is continued for 30 minutes at 80° C. The trimer solution then has an isocyanate content of 30.8%. Thin layer distillation is carried out in a high vacuum to isolate the isocyanurate.

Yield (resin): 568 g (42.6%).

The 75% solution in ethyl glycol acetate has a viscosity of 6576 mPas (25° C.) and an isocyanate content of 12.6%.

Free IPDI (solution): 0.36%.

Example 4

Controlled trimerization to produce particular isocyanate values and the corresponding yields in resin is illustrated by the following examples:

(A) 1332 g of IPDI are heated to 60° C. A total of 10 ml of catalyst solution I is added from a dropping funnel in separate portions of 2.5 ml each. After the first 2.5 ml, the temperature rises to 68° C. within 15 minutes. At that point, a further 2.5 ml of catalyst solution are added to the reaction mixture containing IPDI. The temperature rises to 78° C. 15 minutes after the addition of catalyst, the isocyanate content of the solution is 34.9%. The solution is then stirred for a further 30 minutes at 80° C. and finally distilled by thin layer evaporation (for results see Table I).

(B) In a parallel experiment using 1332 g of isophorone diisocyanate, a further 2.5 ml of catalyst are added 15 minutes after the second addition of catalyst (the NCO-content at this point is 34.7%). After this third addition, the temperature rises from 76° C. to 80° C. 15 minutes after the addition, the isocyanate content of the trimer solution is 32.7%. The solution is then stirred for half an hour at 80° C. and finally worked up by thin layer distillation (for results see Table I).

(C) In another parallel experiment carried out under the same conditions, a further 2.5 ml of catalyst solution are added to the trimer solution which at this point, after the addition of three portions of catalyst, has an isocyanate content of 32.5% and a temperature of 80° C. 15 minutes after this last addition, the isocyanate content is 30.6%, and the temperature rises from 80° C. to 83° C. after the addition of catalyst. After a further 30 minutes stirring, the product is worked up by thin layer distillation as in the previous examples.

(D) In a fourth experiment, a further 1.5 ml of catalyst solution are added after the catalysts carried out as described under (C). The temperature rises by about 2° C. to 84° C. and the isocyanate content falls from 30.5% to 29%. After a further 30 minutes stirring at 80° C., the product is worked up by thin layer distillation.

TABLE I

| Experiment | NCO-content after trimerization | Yield (resin) | Viscosity (25° C.) (75% solution) |
|---|---|---|---|
| A | 34.9% | 250g (18.8%) | 2040 mPas |
| B | 32.7% | 350g (27%) | 3520 mPas |
| C | 30.6% | 545g (41%) | 5350 mPas |
| D | 29.0% | 680g (51%) | 8730 mPas |

Example 5

50 kg of IPDI are introduced into a stirrer vessel and heated to 55° C. 180 ml of catalyst solution I are added from a dropping funnel containing a total of 375 ml. The temperature rises and reaches its first maximum of 65° C. within 20 minutes. Trimerization continues to be catalyzed by two further additions of 75 ml each of the solution base, and the temperature rises from 65° to 72° C. after the first addition and from 72° to 80° C. after the second. After the reaction mixture has been stirred for a further 15 minutes, the isocyanate content is 32.9% and the temperature has fallen to 75° C. A further 50 ml of catalyst solution are added to obtain the desired isocyanate content. The temperature then rises by 3° C. to 78° C. Stirring is continued for a further half hour and the solution of trimer, which has an isocyanate content of 31.1%, is worked up by thin layer distillation.

Yield (resin): 16.5 kg (35%).
75% solution in ethyl glycol acetate:
Viscosity: 6500 mPas (25° C.);
NCO-content: 12.6%;
Free IPDI: 0.22%.

Example 6

1332 g (6 mol) of IPDI are introduced into a three-necked flask and heated to 60° C. Catalyst solution II is added portionwise from a dropping funnel containing a total of 20 ml solution, the first portion added amounting to 10 ml. The temperature rises to 67° C. within 20 minutes. When this maximum has been reached, a further 5 ml of solution are added so that the temperature rises to 72° C. The isocyanate content of the trimer solution is then 33.5%. After the addition of a further 3 ml of catalyst solution, an end value of 30.3% is obtained, the temperature having finally risen to 78° C. Stirring is subsequently continued for one hour at 80° C. and the product is then worked up by thin layer distillation in a high vacuum.

Yield (resin): 550 g (41.3%).
75% solution in ethyl glycol acetate:
Viscosity: 5750 mPas (25° C.);
Isocyanate content: 12.8%;
Free IPDI: 0.43%.

Example 7

Catalyst Solution III is used in this Example. 8 ml of this solution are first added from a dropping funnel to 1332 g (6 mol) of IPDI contained in a three-necked flask at 60° C. The temperature then rises to 67° C. within 20 minutes. As in the previous Example, catalysis is continued by portionwise addition of catalyst, each time using 2.5 ml. After three such additions, when the temperature finally reaches 79° C., the isocyanate content of the solution is 31.5%. Stirring is continued for half an hour and the product is finally worked up by thin layer distillation in a high vacuum. The resin thereby obtained is dissolved to form a 75% solution in ethyl glycol acetate.

Yield (resin): 450 g (33.8%).
Viscosity (solution): 4040 mPas (25° C.).
NCO-content (solution): 12.9%.
Free IPDI (solution): 0.3%.

Example 8

The process is carried out similarly to Example 7 using catalyst solution IV. 1332 g (6 mol) of IPDI are heated to 80° C. and a total of 8 ml of catalyst solution is added in two portions of 3 ml and one portion of 2 ml. The temperature is 95° C. after the third addition. The isocyanate content of the trimer solution is then 31.4%. The mixture is then stirred for half an hour at 90° C. and finally worked up by thin layer distillation in a high vacuum.

Yield (resin): 510 g (38%).
75% solution in ethyl glycol acetate:
Viscosity: 7500 mPas (25° C.);
NCO-content: 12.3%;
Free IPDI: 0.27%.

Example 9

50 kg of a mixture of IPDI and 11 ml of catalyst solution I per 1332 g of IPDI are introduced continuously by means of a metering pump into a reaction vessel which is heated to 75° C. The pump output is 11.1 liters per hour. The isocyanate content of the reaction solution becomes established at 31%. After 4.5 hours, the total quantity of the mixture of IPDI and catalyst solution has been added. The reaction mixture is then heated to 80° C. and stirred for a further half hour at this temperature. The final isocyanate content is then 30.5%. The trimer solution is worked up by thin layer distillation in a high vacuum and the resin is then dissolved to form a 70% solution in a 1:1 mixture of xylene/ethyl glycol acetate.

Yield (resin): 18.2 kg (36%).
Viscosity (solution): 1370 mPas (20° C.);
NCO-content (solution): 11.5%;
Free IPDI: 0.25%.

Example 10

As a comparison experiment, trimerization of isophorone diisocyanate is carried out with sodium phenolate according to Example 1 of British Pat. No. 1,386,399.

(a) 3 g of sodium phenolate were dissolved in 201 g of butyl acetate in a three-necked flask under nitrogen at room temperature and 600 g of IPDI were added. Trimerization set in spontaneously during the addition of IPDI so that a temperature of 120° C. was reached within a few moments in spite of the reaction mixture being cooled with ice. When the mixture had been cooled to 90° C., stirring was continued at this temperature but the experiment was terminated after 2 hours because the viscosity of the reaction product was then too high. After the reaction had been stopped, 25 g of a 5% solution of phosphoric acid in ethyl glycol acetate was added and the reaction mixture cooled to room temperature; a reddish-brown, solid, resinous product was obtained.

(b) The experiment was repeated, the phenolate solution which was the first component to be introduced into the reaction flask, was cooled with a mixture of ice and water, and the IPDI was in this case added all at once so that a high dilution of catalyst solution could be obtained immediately. The temperature reached 90° C.

in less than 5 minutes. By alternate "removal of cooling bath" and cooling, the temperature could be stabilized at 90° C. after about 15 minutes. After a further 4 hours stirring, the reaction was stopped and the reaction product cooled to room temperature. A brownish colored solution which had a viscosity of 150,000 mPas (25° C.) was obtained.

(c) The experiment was repeated with a smaller quantity of catalyst. 67 g of butyl acetate were added to 0.5 g of sodium phenolate under an atmosphere of nitrogen and the reaction mixture was cooled with ice/water. 200 g of IPDI was then rapidly added. The temperature rose to 60° C. within a short time in spite of the ice bath. After removal of the cooling means, the temperature rose to 72° C. At 90° C., stirring was continued for 4 hours and the reaction was then stopped with a phosphoric acid solution in ethyl glycol acetate (4.2 g, 5% solution). A brownish colored solution which had a viscosity of 24,500 mPas (25° C.) and an isocyanate content of 10.2% was obtained. The monomeric IPDI content determined by analysis was found to be 3.0%.

(d) In a further experiment, the quantity of catalyst was yet again reduced, and 200 g of IPDI were added to 0.2 g of sodium phenolate in 67 g of butyl acetate by the same method. The reaction, which started at room temperature, reached a temperature maximum of 48° C. after the addition of IPDI. Heating was continued to 90° C. and the reaction mixture was stirred for 4 hours at this temperature. The isocyanate content of the solution was then 19.4%. There was no substantial drop in this value even after one more hour at 90° C. A further quantity of catalyst was therefore added to the trimer solution, in this case 0.5 g of sodium phenolate in 10 ml of butyl acetate. It was surprisingly found that this subsequent catalysis resulted in an only slight rise in temperature by 2° C. After a further 3 hours stirring at 90° C., the isocyanate content of the solution was 18.8%. Since the reaction product had by this time a dark brown color, the experiment was stopped.

The reaction "(c)" which gave relatively the best results, was repeated several times. It was found that reliable reproduction was not possible and that the viscosity of the solutions was many times higher. In one repetition, it was found that trimerization virtually failed to take place in spite of identical conditions. The end product had a viscosity of 100 mPas/25° C.

Example 11

13.32 kg of IPDI are mixed with 65 ml of catalyst solution I at room temperature (23° C.). IPDI is introduced into a laboratory cascade consisting of three 2 liter stirrer vessels with overflow. The above mentioned mixture is pumped at the rate of 3.25 liters per hour into the first stirrer vessel which is maintained at 75° C. To complete the reaction, the product is transferred from this vessel to the second reactor, which is maintained at 85° C. The average residence time in the two cascade vessels is about 90 minutes. In the third reactor, the catalyst is inactivated at 120° C. The isocyanate content in the last outflow is 29%. The crude product is introduced into a thin layer evaporator.

Yield (resin): 48%.
75% solution in ethyl glycol acetate:
Viscosity (20° C.): 4937 mPas;
NCO-content: 12.5%;
Free IPDI: 0.3%.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. A process for the preparation of polyisocyanates containing isocyanurate groups which are soluble in lacquer solvents comprising
   (a) partially trimerizing the isocyanate groups of 1-isocyanato-3,3,5-trimethyl-5-isocyanatomethylcyclohexane in the presence of catalyst(s) which are inactivated by heat and which accelerate the trimerization of isocyanate groups and
   (b) thermally deactivating the catalyst(s), characterized in that the catalyst(s) used are quaternary hydroxyl alkyl ammonium hydroxides containing at least one hydroxy alkyl group.

2. The process of claim 1, wherein the catalyst is used in a quantity of from about 0.01 to 1% by weight, based on the weight of diisocyanate to be trimerized.

3. The process of claim 1, wherein the quaternary hydroxy alkyl ammonium hydroxides containing at least one hydroxy alkyl group correspond to the following formula:

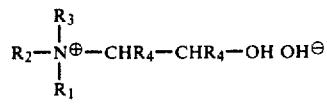

wherein
$R_1$, $R_2$ and $R_3$ are the same or different, represent alkyl groups with about 1 to 20 carbon atoms which may be substituted with hydroxyl groups, cycloalkyl groups with about 4 to 15 carbon atoms which may be substituted with hydroxyl groups, aralkyl groups with about 7 to 15 carbon atoms which may be substituted with hydroxyl groups or aryl groups with about 6 to 15 carbon atoms which may be substituted with hydroxyl groups, and two of the aforesaid groups, $R_1$, $R_2$ and $R_3$ may also combine with the nitrogen atom and optionally with an oxygen atom or another nitrogen hetero atom to form a heterocyclic ring containing about 4 to 6 carbon atoms, the groups $R_1$, $R_2$ and $R_3$ each representing ethylene groups which form a bicyclic triethylene diamine structure together with the quaternary nitrogen atom and another tertiary nitrogen atom;

$R_4$ represents hydrogen and/or an alkyl group with about 1 to 12 carbon atoms, a cycloalkyl group with about 5 to 7 carbon atoms, an aralkyl group with about 7 to 10 carbon atoms, an aryl group with about 6 to 12 carbon atoms or a group of the formula $R_5$—O—$(CH_2)_n$ in which $R_5$ represents hydrogen, an alkyl group with about 1 to 12 carbon atoms, a cycloalkyl group with about 4 to 10 carbon atoms, an aralkyl group with about 7 to 10 carbon atoms or an aryl group with about 6 to 10 carbon atoms; and n is an integer of from about 1 to 6.

4. The process of claim 3, wherein $R_1$, $R_2$ and $R_3$ represent the same or different alkyl groups having from about 1 to 4 carbon atoms and $R_4$ represents hydrogen.

5. The process of either claim 1 or 4, wherein the catalyst is N,N,N-trimethyl-N-(2-hydroxyethyl)-ammonium hydroxide.

6. The process of claim 1, wherein the reaction is carried out at temperatures between about 30° and 90° C.

7. The process of claim 1, wherein prior to catalysis the diisocyanate is preheated between about 40° and 110° C.

8. The polyisocyanates containing isocyanurate groups produced by the process of claim 1.

9. In a process for the production of polyurethane lacquers from polyisocyanates, the improvement which comprises using polyisocyanates containing isocyanurates prepared by the process of claim 1.

10. The process of claim 9, wherein the polyisocyanates containing isocyanurate groups are blocked with blocking agents for isocyanate groups.

11. A polyisocyanate mixture produced by a process comprising
(a) reacting 1-isocyanato-3,3,5-trimethyl-5-isocyanatomethyl-cyclohexane in the presence of catalyst(s) which are inactivated by heat and which accelerate the trimerization of isocyanate groups,
(b) thermally deactivating the catalyst(s), and
(c) removing substantially all of the remaining unreacted monomeric-1-isocyanato-3,3,5-trimethyl-5-isocyanatomethyl-cyclohexane by high vacuum thin layer distillation, characterized in that the catalyst(s) used are quaternary hydroxy alkyl ammonium hydroxides containing at least one hydroxy alkyl group.

12. A process for the preparation of polyisocyanates containing isocyanurate groups which when dissolved at a concentration of about 75% by weight in ethylglycol acetate have a viscosity of at the most about 50,000 mPa.s at 25° C., an isocyanate content of about 9.5 to 15.5% by weight and a free diisocyanate content of below about 3% by weight, which comprises partially trimerizing the isocyanate groups of 1-isocyanato-3,3,5-trimethyl-5-isocyanatomethyl-cyclohexane at temperatures between about 30° and 90° C. in the presence of quaternary hydroxy alkyl ammonium hydroxides containing at least one hydroxy alkyl group, thermally deactivating the catalyst and distilling off unreacted excess 1-isocyanato-3,3,5-trimethyl-5-isocyanatomethylcyclohexane.

* * * * *